United States Patent
Lenigk et al.

(10) Patent No.: US 9,480,981 B2
(45) Date of Patent: Nov. 1, 2016

(54) SAMPLE COLLECTION AND TRANSFER DEVICE

(71) Applicant: General Electric Company, Schenectady, NY (US)

(72) Inventors: Ralf Lenigk, Niskayuna, NY (US); Erin Jean Finehout, Clifton Park, NY (US); Xuefeng Wang, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 97 days.

(21) Appl. No.: 14/341,074

(22) Filed: Jul. 25, 2014

(65) Prior Publication Data

US 2016/0023206 A1  Jan. 28, 2016

(51) Int. Cl.
*B01L 3/02* (2006.01)
*B01L 3/00* (2006.01)
*C12Q 1/68* (2006.01)

(52) U.S. Cl.
CPC ........ *B01L 3/5023* (2013.01); *B01L 3/502715* (2013.01); *B01L 3/561* (2013.01); *C12Q 1/6806* (2013.01); *B01L 3/0258* (2013.01); *B01L 3/0262* (2013.01); *B01L 2200/027* (2013.01); *B01L 2200/0605* (2013.01); *B01L 2300/069* (2013.01);

(Continued)

(58) Field of Classification Search
CPC .................. B01L 2200/16; B01L 2300/0887; B01L 2200/0642; B01L 2300/087; B01L 2300/0636; B01L 2300/0838; B01L 2300/0816; B01L 2400/0406; B01L 2200/026; B01L 3/5023; B01L 3/563; B01L 9/527; B01L 3/502715; B01L 3/561; B01L 2200/0605; B01L 2200/027; B01L 3/0262; B01L 3/0258; B01L 2300/161; B01L 2300/069; G01N 35/1002; C12Q 1/6806
See application file for complete search history.

(56) References Cited

U.S. PATENT DOCUMENTS

| 4,301,414 A | 11/1981 | Hill et al. |
| 4,756,884 A | 7/1988 | Hillman et al. |
| 5,049,487 A | 9/1991 | Phillips et al. |

(Continued)

FOREIGN PATENT DOCUMENTS

| WO | 9858260 A1 | 12/1998 |
| WO | 2012027048 A2 | 3/2012 |
| WO | 2013144743 A1 | 10/2013 |

OTHER PUBLICATIONS

"Evaluation Report of the ACCU-CHEK® Comfort Curve Test Strip as a Plasma-like Test Strip", ACCU-CHEK, 2008, 16 Pages.

(Continued)

*Primary Examiner* — Dennis M White
(74) *Attorney, Agent, or Firm* — Eileen B. Gallagher

(57) ABSTRACT

An integrated device for a sample collection and transfer is provided. The integrated device comprises a capillary channel disposed between a first layer and a second layer, wherein the first layer comprises a hydrophilic layer comprising a fluid inlet for receiving a sample fluid to the capillary channel, wherein the capillary channel comprises an inner surface and an outer surface and an outlet for driving out the sample fluid. The device further comprises an interface assembly comprising: a third layer, a fourth layer, a fifth layer, and a flow path. The interface assembly is disposed on the outer surface of the capillary, at a determining position relative to the outlet, such that the capillary is in contact with the third layer of the interface assembly and the outlet is in contact with the flow path of the interface assembly for driving out the sample fluid from the integrated device.

32 Claims, 7 Drawing Sheets

(52) U.S. Cl.
CPC ... *B01L 2300/0887* (2013.01); *B01L 2300/161* (2013.01); *B01L 2400/0406* (2013.01)

(56) References Cited

U.S. PATENT DOCUMENTS

| | | |
|---|---|---|
| 7,264,627 B2 | 9/2007 | Perez |
| 7,276,146 B2 | 10/2007 | Wilsey |
| 7,488,298 B2 | 2/2009 | Patel et al. |
| 7,670,301 B2 | 3/2010 | Roe |
| 8,083,688 B2 | 12/2011 | Roe |
| 8,333,715 B1 | 12/2012 | Alferness |
| 2001/0039057 A1 | 11/2001 | Douglas et al. |
| 2001/0053334 A1 | 12/2001 | Chen et al. |
| 2003/0060730 A1 | 3/2003 | Perez |
| 2011/0008223 A1* | 1/2011 | Tsao ............... B01L 3/502715 422/502 |
| 2011/0124984 A1 | 5/2011 | Rostaing |
| 2012/0000299 A1 | 1/2012 | Buechner |
| 2013/0026037 A1 | 1/2013 | Bryan |

OTHER PUBLICATIONS

"Collection Procedures for Capillary Blood Lead Specimens", Michigan Department of Community Health Bureau of Laboratories Division of Chemistry & Toxicology Trace Metals Lead Section, pp. 1-12.

PCT Search Report and Written Opinion issued in connection with corresponding PCT Application No. PCT/EP2015/066532 on Sep. 28, 2015.

PCT Search Report and Written Opinion issued in connection with related PCT Application No. PCT/EP2015/066530 on Sep. 28, 2015.

* cited by examiner

SAMPLE COLLECTION AND TRANSFER DEVICE

FIELD

The invention relates to collection and transfer of biological samples, and more particularly to devices configured to collect, transfer and store the biological samples to a substrate for analysis.

BACKGROUND

Devices and related methods for collection and transfer of a biological sample fluid (such as blood) have been widely used for a variety of applications, such as analyte-detection, sensing, forensic and diagnostic applications, genome sequencing, and the like. In some applications, a quantitative measurement is desired, such as measuring a concentration of a drug metabolite in the blood, a titer of a virus in a sample, a level of mRNA in a sample and the like. To achieve accurate results for these applications, preserving the structural and functional integrity of the biomolecules present in a biological sample fluid is a primary requirement. A method for preserving integrity of the sample is to store the sample on a stabilizing substrate or a membrane. Measurement of the volume of a sample is also required to achieve accurate results for different quantitative analyses.

The most widely used method of collecting blood sample is by venipuncture, which requires sterile equipment, collection tubes and a trained phlebotomist for drawing the blood sample. An alternate method is skin piercing such as finger stick using a lancet. After piercing, a suitable device and a method is required for collection and/or transfer of the blood sample to a storage substrate or membrane. For these devices, it is necessary to ensure that the correct amount of blood is collected, a blood sample is completely transferred to a substrate, the blood is transferred to a correct location on a substrate, and the blood is applied evenly to a substrate. Application of a sample to a substrate may be achieved by using a capillary for collection followed by sample transfer to the substrate. However, the transfer may not occur completely if a gap exists between the capillary and the membrane. Further, the sample may not be applied evenly if the placement of the capillary is not accurate relative to the substrate or the flow rate of the sample exiting the capillary is controlled appropriately. Therefore, a skilled person is required for careful handling of the device and for collection and transfer of the blood sample.

Devices and methods that allow a person with an average skill to quickly collect and transfer a specific and consistent amount of sample to a correct location on a substrate with an even distribution are highly desirable. The devices and methods may further facilitate an automated sample analysis by applying an accurate amount of sample at a desired position on the substrate.

BRIEF DESCRIPTION

In one embodiment, an integrated device for a sample collection and transfer is provided, wherein the device comprises a capillary channel disposed between a first layer and a second layer, wherein the first layer comprises a hydrophilic layer comprising a fluid inlet for receiving a sample fluid to the capillary channel, wherein the capillary channel comprises an inner surface and an outer surface; and an outlet for allowing the sample fluid to flow out of the capillary channel; and an interface assembly comprising: a third layer comprising an adhesive material, a fourth layer comprising a hydrophilic material, a fifth layer comprising a patterned adhesive material, and a flow path, wherein the third layer is disposed on the fourth layer and the fourth layer is disposed on the fifth layer; wherein the interface assembly is disposed on the outer surface of the capillary, at a determining position relative to the outlet, such that the capillary is in contact with the third layer of the interface assembly and the outlet is in contact with the flow path of the interface assembly for transferring the sample fluid out of the integrated device.

In another embodiment, a system is provided, wherein the system comprises a substrate and an integrated device. The integrated device comprises a capillary channel disposed between a first layer and a second layer, wherein the first layer comprises a hydrophilic layer comprising a fluid inlet for receiving a sample fluid to the capillary channel and wherein the capillary channel comprises an inner surface and an outer surface; and an outlet connected to the capillary channel; and an interface assembly comprising: a third layer comprising an adhesive material, a fourth layer comprising a hydrophilic material, a fifth layer comprising a patterned adhesive material and a flow path, wherein the third layer is disposed on the fourth layer and the fourth layer is disposed on the fifth layer; wherein the interface assembly is disposed on the outer surface of the capillary, at a determining position relative to the outlet, such that the capillary channel is in connection with the flow path of the interface assembly. The integrated device is operatively coupled to the substrate such that substrate is in contact with the interface assembly for transferring the sample fluid from the integrated device to the substrate.

In yet another embodiment, a method for sample collection and transfer comprises providing an integrated device, wherein the device comprises: a capillary channel disposed between a first layer and a second layer, wherein the first layer comprises a hydrophilic layer comprising a fluid inlet for receiving a sample fluid to the capillary channel, wherein the capillary channel comprises an inner surface and an outer surface; and an outlet for allowing the fluid to flow out from the device; and an interface assembly comprising: a third layer comprising an adhesive material, a fourth layer comprising a hydrophilic material, a fifth layer comprising a patterned adhesive material, and a flow path, wherein the third layer is disposed on the fourth layer and the fourth layer is disposed on the fifth layer; wherein the interface assembly is disposed on the outer surface of the capillary, at a determining position relative to the outlet, such that the capillary channel is in connection with the flow path of the interface assembly. The method further comprises contacting the integrated device to a substrate comprising an absorbent material; applying a fluid sample to the capillary inlet of the integrated device, wherein the fluid sample is transported from the inlet to the outlet of the capillary; and transferring the fluid from the integrated device to the substrate through the flow path of the interface assembly; wherein the sample collection and transfer is achieved at least in 10 seconds.

In yet another embodiment, a method for sample collection and transfer, comprises providing an integrated device, wherein the device comprises a capillary channel disposed between a first layer and a second layer, wherein the first layer comprises a hydrophilic layer comprising a fluid inlet for receiving a sample fluid to the capillary channel, wherein the capillary channel comprises an inner surface and an outer surface; and an outlet for driving out the sample fluid; and an interface assembly comprising: a third layer comprising an adhesive material, a fourth layer comprising a hydrophilic material, a fifth layer comprising a patterned adhesive material, and a flow path, wherein the third layer is disposed on the fourth layer and the fourth layer is disposed on the fifth layer; wherein the interface assembly is disposed on the outer surface of the capillary, at a determining position relative to the outlet, such that the capillary channel is in connection with the flow path of the interface assembly; contacting the device to the substrate comprising an absorbent material; applying a fluid sample to the capillary inlet of the integrated device, wherein the fluid sample is transported from the inlet to the outlet of the capillary; and transferring the fluid from the integrated device to the substrate through the flow path of the interface assembly, wherein the sample collection and transfer is achieved in at least 10 seconds; and analyzing a portion of the substrate comprising the fluid sample transferred from the device.

DRAWINGS

These and other elements and aspects of the present specification will become better understood when the following detailed description is read with reference to the accompanying drawings in which like characters represent like parts throughout the drawings, wherein.

Figure 6A:
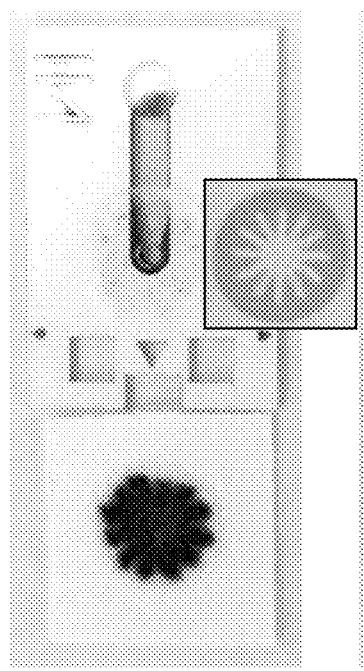
FIGS. 6A, 6B and 6C are a series of images of integrated devices using different gasket designs, after transferring samples to respective substrates. Different gasket designs are shown in inset of the respective devices.
Figure 6B:
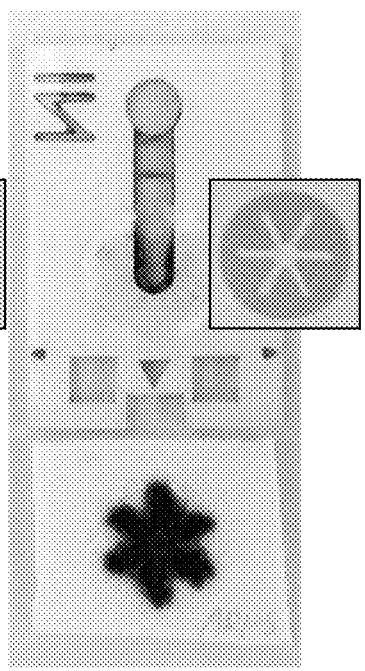
Figure 6C:
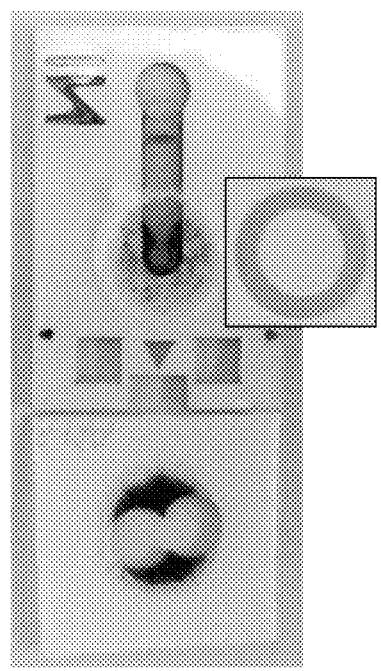

FIGS. 6 D, 6E and 6F are series of images showing substrates after sample transferred therein using the devices of FIGS. 6A, 6B and 6C, respectively.

Figure 7:
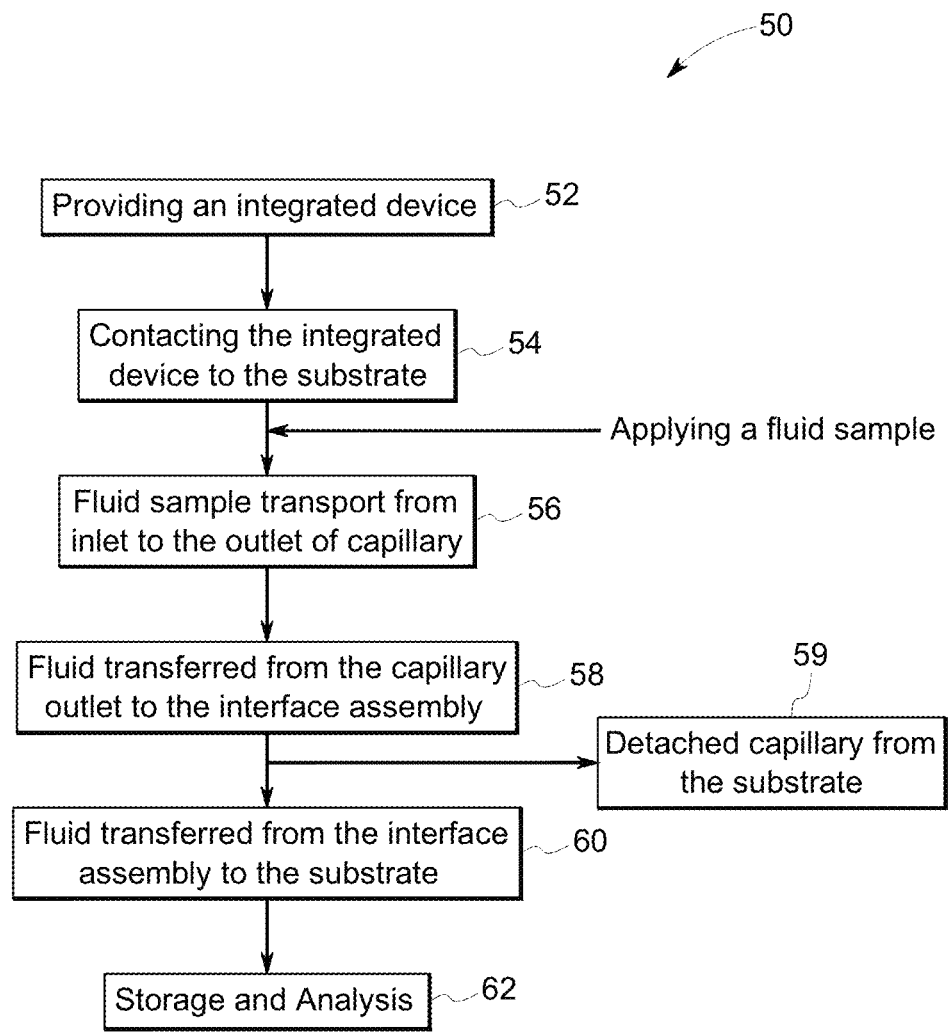

FIG. 7 is a flow chart of an example method of using the integrated device for collection and transfer of sample.

DETAILED DESCRIPTION

Embodiments of the present specification relate to methods and devices for collecting a biological sample and transferring the biological sample from the device to a substrate or a part of another device or system. In some embodiments, the device, as referred to herein as an "integrated device," for collection and transfer of a sample is configured such that it facilitates safe collection and efficient transfer of the sample to a substrate, while preventing any undesirable contact of the user with the sample or substrate while transferring the sample from the integrated device to the substrate.

One or more embodiments of an integrated device for a sample collection and transfer comprise two components, a capillary channel and an interface assembly. The integrated device may include a multilayered structure. The device may be configured to house a capillary and an interface assembly for sample collection and transfer to a substrate.

In embodiments of the integrated device, the first component is a capillary channel, which is disposed between a first layer and a second layer, wherein the first layer comprises a hydrophilic layer comprising a fluid inlet for receiving a sample fluid into the capillary channel. The capillary channel may comprise an inner surface and an outer surface; and an outlet for allowing the sample fluid to flow out of the channel. The capillary channel may be configured to provide a fluidic connection between the sample receiving inlet and the interface assembly through the outlet.

The integrated device of these embodiments further comprises an interface assembly comprising: a third layer comprising an adhesive material, a fourth layer comprising a hydrophilic material, a fifth layer comprising a patterned adhesive material, and a flow path. As noted, the interface assembly may comprise three layers, such as a third layer, a fourth layer and a fifth layer, which are disposed sequentially, for example, the third layer is disposed on fourth layer, the fourth layer is disposed on the fifth layer. The interface assembly may be disposed on the outer surface of the capillary, at a determining position relative to the outlet, such that the capillary is in contact with the third layer of the interface assembly and the outlet is in contact with the flow path of the interface assembly for transferring the sample fluid out of the integrated device.

As noted, the capillary channel is disposed between a first layer and a second layer, wherein the channel may be defined as a cavity formed in a middle layer that is disposed between the first layer and the second layer of the capillary. In some embodiments, the first layer and the second layer of the capillary comprise a hydrophilic polymer film. In some embodiments, the first layer may be a plastic layer comprising a hydrophilic treatment, coating or film. The second layer may be the same as the first layer with a hydrophilic treatment, coating or film. In some embodiments, the second layer comprises a plastic material, wherein the surface properties of the layer are conducive for liquid transport based on the hydrophilicity of the first layers. The middle layer, where the channel is created, may be a polymeric layer.

As noted, the capillary channel may comprise a cavity, wherein the cavity is defined in a middle layer disposed between the first layer and the second layer. In some embodiments, a pre-cut layer is disposed as a middle layer between the first layer and the second layer and the three layers are laminated together. In some other embodiments, before formation of the cavity or the channel, the first layer, second layer and middle layer may be laminated together to form a multilayered monolithic structure. In the monolithic capillary structure, the capillary channel or a cavity may be formed by patterning the middle layer. The cavity may form in desired shapes and dimensions (length, width, height) by drilling the middle layer, which is defined as the capillary channel. The maximum volume of the cavity may be defined as a channel capacity.

The channel (or cavity), inlet and outlet of the capillary may be formed by a process but is not limited to, laser cutting, rotation cutting, ballistic pressing, injection molding, ballistic punching or combination thereof. In one embodiment, the capillary channel or a cavity may be formed by laser cutting of the middle layer. In another embodiment of the integrated device, the capillary channel is created by injection molding. In another embodiment of the integrated device, the capillary channel is created by ballistic punching. The inlet and the outlet holes may be laser drilled on the first layer or on the second layer.

In some other embodiments, the capillary channel comprises two layers, a first layer and a second layer, wherein the channel cavity is created either in the first layer or in the second layer by partial removal of the materials from the respective layers. In another embodiment of the integrated device, the capillary channel comprises two layers, a first layer and a second layer, wherein the channel cavity is created by partial removal of the materials from both of the first layer and the second layer.

The capillary may be made from low-cost and non-fragile materials. The capillary channel may be made of a material selected from polymer, metal, glass or combinations thereof. The capillary channel may be made of a variety of polymeric films, such as the films commonly used in the fabrication of laminated devices. In one or more embodiments, the capillary comprises a plurality of plastic layers, which are laminated together and formed a channel. The laminated capillary is advantageous compared to a glass capillary or any other hard capillary tube, as the laminated capillary has reduced chance of breaking compared to glass or rigid polymer materials. Further, the laminated capillary is inexpensive to fabricate, and may easily be integrated with a substrate.

As noted, the capillary may have a laminated multilayered structure, including a first layer of hydrophilic polymer film, a middle polymeric layer and a second layer of hydrophilic polymer film. The first and second hydrophilic polymer layers of the capillary may be made of a hydrophilic polyester film, such as hydrophilic polyester film 9660 from 3M™. The hydrophilic polyester film is stable and non-leachable. The thickness of both first hydrophilic polymer layer and the second hydrophilic polymer layer are same or similar. In some embodiments, the first and second hydrophilic polymer layers are about 0.01 to 0.5 mm thick. In one exemplary embodiment, the first and second hydrophilic layers are about 0.173 mm thick.

The middle layer may comprise a polycarbonate resin, such as Lexan™ laminating film with high moisture resistance. The middle layer may be thicker than the first and/or second hydrophilic polymer layers. In some embodiments, the middle layer is 0.02 to 1.0 mm thick. In one exemplary embodiment, the middle layer is 0.25 mm thick.

Adhesive films may be used to attach the layers, such as first layer, middle layer and second layer to each other. In some embodiments, double sided adhesive films are used to integrate the layers to form the capillary channel. For example, AR 8939 double sided adhesive film (from Adhesive Research) of 0.125 mm thick was used in between layers for bonding the layers to form the capillary channel. The fluidic capillary channel may be created, for example, by laser cutting of the middle layer and the adhesive layers.

The capillary channel may comprise an inner surface and an outer surface. The capillary interior may comprise four walls; such as a top-wall, a bottom-wall and two side-walls. The hydrophilic layers of the capillary channel may allow creating a capillary force using the hydrophilic side-walls.

The capillary channel of the integrated device enables reproducible sample collection through an inlet and sample transfer through an outlet to a substrate. As noted, the integrated device may include a fluid inlet at the first layer of the capillary for receiving a sample fluid. The inlet may have an access to the capillary channel, wherein the fluid inlet of the capillary may provide a fluidic contact between the fluid inlet and the fluid outlet. The inlet may further have a fluidic connection to the interface assembly.

In some embodiments, the device further comprises a hydrophilic pad adjacent to the inlet to facilitate receiving a sample fluid to the capillary using a hydrophilic force. The hydrophilic pad may also refer to herein as a "loading pad". In these embodiments, the area of the first hydrophilic layer expands outside of the capillary inlet to facilitate the sample collection. The "loading pad" is more useful when the sample volume is larger, such as in a range of 10-100 μl The sample may be loaded faster and more conveniently using the loading pad compared to a case where the inlet does not contain a loading pad. The requirement of holding the capillary inlet to the source of a blood-drop for sample intake, spilling of a blood sample or incomplete transfer of blood from the source to the capillary inlet may be avoided by using the loading pad.

Further, as noted, the integrated device may include a fluid outlet for allowing the fluid to flow out from the device. The fluid outlet may be located on the capillary channel for making a path of the outgoing fluid sample received from the inlet. In one example, the fluid outlet has an access to the substrate when the substrate is coupled to the integrated device, either directly or indirectly. The outlet may have access to the substrate through the flow path of the interface assembly.

In some embodiments, the first layer of the capillary channel may comprise a fluid inlet and a fluid outlet. In some other embodiments, the second layer of the capillary channel comprises a fluid outlet, wherein the first layer comprises a fluid inlet. The fluid outlet may be provided through an opening in the first layer or second layer of the capillary channel corresponding to the flow path of the interface assembly, wherein the interface assembly is further aligned with the substrate. As noted, in some embodiments, the interface assembly is disposed on the outer surface of the capillary at a determining position relative to the outlet, such that the outlet is in contact with the flow path of the interface assembly. In these embodiments, the determining position is configured to align the outlet of the capillary with the flow path of the interface assembly. The fluid outlet may be opened to the flow path, which further connects the outlet to the substrate. The fluid inlet and outlet may allow the device to be connected to an internally coupled substrate or an externally located substrate or device for sample storage, extraction or combinations thereof.

In some embodiments, the capillary channel comprises an inlet with a loading pad having a first diameter, a capillary has a width (capillary width) and an outlet with a second diameter, wherein the first diameter is greater than the capillary width and the capillary width is greater than the second diameter. In these embodiments, as the capillary width is greater than the diameter of the outlet (second diameter), the outlet is completely surrounded by the capillary channel. As the outlet diameter is smaller than the capillary channel width, it allows the fluid sample to flow around the outlet and enter the outlet from all sides. This feature increases the flow rate of the fluid that flows out of the capillary, which further prevents clogging of the outlet or flow path during fluid flow.

The capillary dimensions, such as length, height or width of the capillary channel may be selected to allow collection of a pre-determined volume of sample and efficient fluid sample transfer before any structural or functional changes occur to the components of the sample fluid. The collection and transfer time of the fluid, such as blood may be optimized such that the integrated device transfers the blood sample before blood coagulation starts. For example, an untreated blood sample is transferred through the capillary of the integrated device within 1 to 2 minutes after receiving the blood sample from a finger stick. The time for collection and transfer of the sample depends on the volume of the sample to be transferred.

As noted, a loading pad having a first diameter located adjacent to the capillary inlet, the capillary channel has a capillary width and the outlet has a second diameter. In some embodiments, the first diameter of the loading pad is in a range between 3 and 50 mm and the second diameter of the capillary channel outlet is in a range between 0.4 and 10 mm. In these embodiments, the channel width is in a range of 0.5 to 20 mm, and the channel height is in a range of 0.05 mm to 2 mm. In one embodiment, the loading pad has a diameter of about 6 mm, and an outlet has a diameter of 2.25 mm. In this embodiment, the channel width is about 4.25 mm, and the channel height is about 0.5 mm. Based on practical considerations, the capillary may be straight or curved structure. In some embodiments, the capillary may be a serpentine channel. In one embodiment, the capillary channel has a length in a range from 5 mm to 200 mm. In some embodiments, the outlet is connected to a storage substrate through the flow path, wherein the integrated device ensures efficient transfer of fluid sample to a well-defined area of the substrate with uniform sample application. The integrated device also ensures preventing the fluid from wicking along the interface assembly. In some embodiments, the capillary channel may contain a volume of sample for collection and transfer is between 10 and 100 microliters.

The capillary channels may be configured to provide a fluidic connection between the integrated device and the substrate. The fluid sample in the integrated device may flow from the inlet of the integrated device towards the outlet. Further, the fluid may pass through the outlet of the capillary and enter into the flow path of the interface assembly. The capillary channel and the flow path of an interface assembly may include features to facilitate fluid flow through the interface assembly to a region of interest (e.g., at the center of the applied sample area or sample application zone) of the substrate. The movement of the capillary may be restricted during the sample transfer, which ensures that the applied sample is evenly distributed and not smeared across the surface of the substrate.

In some embodiments of the integrated device, the second component is an interface assembly comprising one or more layers. In some embodiments, the interface assembly comprises three layers. The interface assembly may comprise a third layer comprising an adhesive material, a fourth layer comprising a hydrophilic material and a fifth layer comprising a patterned adhesive material, wherein the third layer is disposed on the fourth layer and the fourth layer is disposed on the fifth layer. The interface assembly may further comprise a passage or a flow path through the third layer, fourth layer and fifth layer.

In some embodiments of the integrated device, the interface assembly is disposed on the outer surface of the capillary. The interface assembly may be disposed at a determining position relative to the outlet of the capillary, such that the capillary is in contact with the third layer of the interface assembly and the outlet opens at the flow path of the interface assembly. In these embodiments, the sample fluid is withdrawn from the capillary channel and entered in the interface assembly flow path and flows out of the integrated device.

As noted, the interface assembly comprises three layers, such as third layer, fourth layer and fifth layer, wherein the layers are formed around the outlet of the capillary, keeping a passage at the center forming a flow path of the interface assembly. In embodiments, wherein the outlet is circular in shape, the layers may be a ring like structure, which has a gap (hole) at the center of the ring. The gap at the center may be aligned with the outlet of the capillary to make a passage for the fluid sample to transfer to a substrate or other device. The rings of the third layer, fourth layer and fifth layer are disposed on one after another respectively, and the aligned gaps of three layers may form the flow path.

In some embodiments, the third layer comprises a pressure sensitive adhesive material. In some embodiments, the pressure sensitive third layer comprises a patterned adhesive film. The pressure sensitive adhesive material may include but is not limited to, acrylics, butyl rubber, ethylene-vinyl acetate (EVA), natural rubber; nitriles; silicone rubbers, styrene block copolymers (SBC), styrene-butadiene-styrene (SBS), styrene-ethylene/butylene-styrene (SEBS), styrene-ethylene/propylene (SEP), styrene-isoprene-styrene (SIS), vinyl ethers and combinations thereof.

The fourth layer may comprise a hydrophilic material comprising polymer. In one embodiment, the fourth layer comprises a hydrophilic plastic material. The fourth layer may comprise a polyester film with hydrophilic coating, such as 3M 9960. A variety of hydrophilic plastic material commonly used in the fabrication of laminated devices may be used for making fourth layer of the interface assembly. The hydrophilic material offers a chemically inert layer for transport of fluid sample through the flow path of the interface assembly. The hydrophilic film also provides a fast and efficient spreading of the fluid sample while transporting from the capillary to the substrate. For example, a hydrophilic plastic film is used for the hydrophilic layer of the interface assembly.

Further, the interface assembly may comprise a fifth layer, wherein the fifth layer comprises a pressure sensitive material. In some embodiments; the fifth layer of pressure sensitive material comprises a gasket. The gasket may be made of a pressure sensitive adhesive material as described above.

In one or more embodiments, the gasket further comprises one or more channels. The gasket may comprise channels, which may have different diameters and length, depending on the requirement. The channels of the gasket allow quick transfer and easy spreading of liquid away from the center of the sample application zone on the substrate. As used herein, the term "sample application zone", refers to an area on the substrate where the fluid sample is disposed or applied on the substrate from the integrated device. A smearing of the applied sample at the sample application zone may be avoided by using the multiple channels on the gasket. The multiple channels help to distribute the fluid sample after applying the sample on the substrate in different directions through the channels and the applied sample does not retain only at the center of the application zone. A larger surface area may prevent clogging, and allows a rapid absorption of liquid sample by the substrate.

In one example, the gasket is a patterned adhesive gasket. The channels may be spread in different directions and form different patterns on the gasket. For example, a plurality of channels form a design of star on the gasket, wherein the channels are spread in different directions from the center of the application zone. The patterned gasket may allow generating a symmetric blood-spot with a reproducible diameter that is centered on the area of sample application zone on the substrate. The use of patterned gasket is desirable for automatic application and downstream processing of the blood-samples on the substrates. In some embodiments, the gasket may be a ring having a diameter between 1 to 50 mm, in one embodiment the gasket ring has a diameter of 10 mm.

In one or more embodiments, the gasket comprises a secondary capillary function by drawing fluid sample, such as blood from the outlet of the capillary channel. The secondary capillary function of the gasket may significantly reduce the time required for the fluid (blood) to transfer to the substrate. For example, the design of the interface assembly reduces the time of transferring sample fluid to at least about 15 seconds instead of 1 minute. Further, the use of gasket in the interface assembly ensures a uniform distribution of the fluid sample on the substrate.

The outgoing fluid sample from the flow path may transfer to the substrate. By way of example, the fluid may be directed towards the substrate for sample storage. The position of attachment of the substrate to the integrated device determines the position on the substrate, such as an FTA card, where the sample is to be transferred from the device.

In one or more embodiments, the integrated device is coupled to a substrate, wherein the integrated device is configured to transfer the sample fluid to the substrate. The integrated device may either be attached directly to the substrate or to a substrate frame that holds the substrate. In some embodiments, the integrated device is further coupled to a substrate frame and a substrate cover. The substrate frame and substrate cover may include features to facilitate efficient fluid transfer to the substrate at a region of interest, e.g., at the center of the substrate.

In some embodiments, the integrated device is packaged with a sample storage substrate, wherein the integrated device is pre-attached to the sample storage substrate. In some other embodiments, the integrated device and substrate are packaged separately, wherein the user may assemble the substrate and the integrated device for sample collection and transfer.

As used the term "substrate", the substrate may refer to any absorbent material which can absorb a fluidic sample, such as blood. In one or more embodiments, the substrate comprises cellulose, nitrocellulose, modified porous nitrocellulose or cellulose based substrates, polyethyleneglycol-modified nitrocellulose, a cellulose acetate membrane, a nitrocellulose mixed ester membrane, a glass fiber, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, glass fiber membranes, quartz fiber membranes, or a combination thereof.

In some embodiments, the substrate comprises one or more dried reagents impregnated therein. The dried reagents may comprise protein stabilizing reagents, nucleic acid stabilizing reagents, cell-lysis reagents or combinations thereof. In one embodiment, the substrate is disposed on a substrate frame. Non-limiting examples of the sample substrate may include a porous sample substrate, Whatman FTA™ card, cellulose card, or combinations thereof.

In some embodiments, the substrate may include at least one stabilizing reagent that preserves at least one biological sample analyte for transport or storage. Non-limiting examples of suitable reagents for the storage media may include one or more of a weak base, a chelating agent, and, optionally, uric acid or a urate salt or simply the addition of a chaotropic salt, alone or in combination with a surfactant. In one embodiment, the sample substrate may have a visual delineation disposed around a transfer area of the sample substrate such that, if the sample storage and extraction device is removed from the assembly or system, an operator may know where the material was deposited without reference to the assembly or system.

An integrated device may be disposable or re-usable. In certain embodiments, an integrated device for sample collection and transfer is a single-use disposable device that is configured to collect the sample and transfer the sample fluid to a substrate and facilitate loading of the fluid sample through desirable areas of the substrate.

The integrated device may be employed in assemblies or systems that are configured to perform one or more of collection, transfer, storage, and analysis of one or more biological samples in a controlled manner. By way of example, the integrated device for sample collection and transfer may be used to collect biologically sourced analytes such as nucleic acids, proteins, and respective fragments thereof.

In some embodiments, a system comprises a substrate; and an integrated device; wherein the integrated device is operatively coupled to the substrate such that substrate is in contact with the interface assembly for transferring the sample fluid from the integrated device to the substrate. The integrated device may be configured such that the device is easily removable from the substrate. The system further comprises a substrate frame having a substrate region configured to receive the substrate. The substrate may be attached to the substrate frame in a way that makes it easy to remove the substrate from the system, and that the substrate frame is designed with a barcode to enable machine processing. The system may further be coupled to an external device, wherein the external device comprises a fluidic device, an analytical instrument, or both.

In some embodiments of the system, the integrated device may be in an operative association with a sample storage and extraction device, which is further coupled to a fluidic device for sample elution and processing via a connected instrument. In one embodiment, the sample collection device may be configured to receive at least one sample at a time. In some embodiments, one or more parts of the single-use disposable integrated device for sample collection and transfer may be configured for one time use to reduce or prevent contamination or spreading of infection via the collected sample. In certain embodiments, the integrated device for sample collection and transfer may be configured for reliable and reproducible collection, transfer and storage of biological samples. In certain embodiments, a percentage of the biological sample transferred from the sample collection device to a sample storage and extraction device may be reproducible.

After collection and transfer of the biological sample, the sample storage device may be configured to store the received sample for further processing and analyzing. In one embodiment, the sample collection and transfer device may be configured to facilitate flow of liquids through a capillary channel and transfers to a desirable area of the substrate. In certain embodiments, the sample collection and transfer device integrated with sample storage unit may further be coupled to another external device for sample elution and processing. In a non-limiting example, the external device may include a fluidic device, an analytical system.

The terms "sample" and "biological sample" may be used herein interchangeably throughout the specification. The biological sample may be blood or any excretory liquid. Non-limiting examples of the biological sample may include saliva, blood, serum, cerebrospinal fluid, semen, feces, plasma, urine, a suspension of cells, or a suspension of cells and viruses. In a non-limiting example, the biological samples may include plant or fungal samples.

In some embodiments, the samples may be collected as a dried sample, which may be hydrated to form a liquid sample and applied to the integrated device for accurate volume of sample collection and transfer to a substrate for further analysis. In one example, the integrated device may be used for collecting dried or liquid biological samples for purposes, such as but not limited to, buccal cell samples, forensic samples (i.e., rehydrated blood, semen, saliva and liquid samples of the same), nasal samples, bacterial or parasite samples, biological samples from animals for veterinary diagnostics or other applications. It should be noted that at the time of collection, the biological samples may or may not exist in a biological body from where the sample originated. By way of example, the biological sample may include a blood sample splattered on a floor of a crime scene.

Figure 1A:
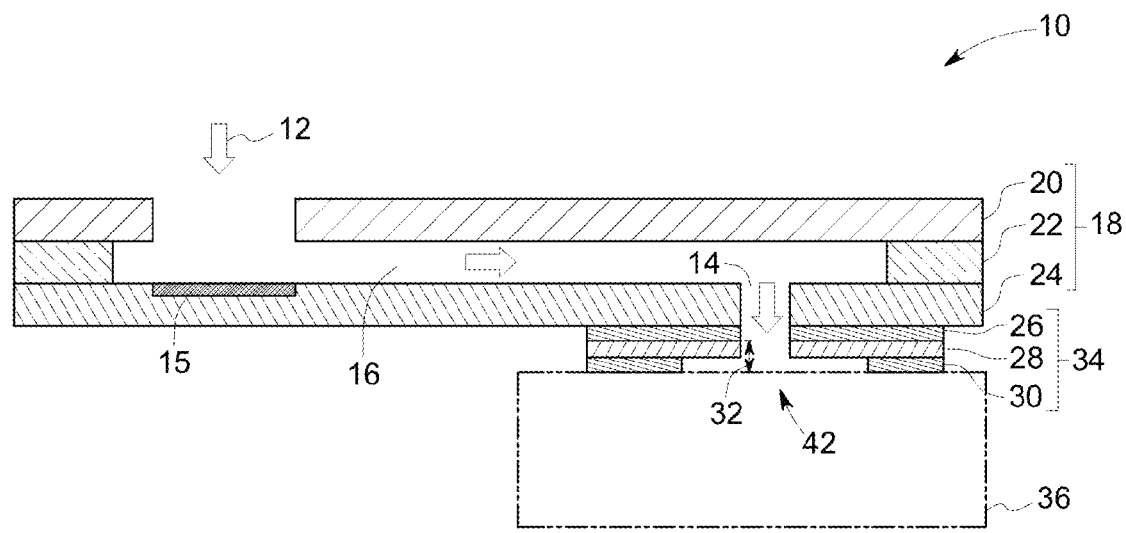
FIG. 1A is a schematic representation of a cross-sectional view of an example embodiment of an integrated device for sample collection and transfer.
Figure 1B:
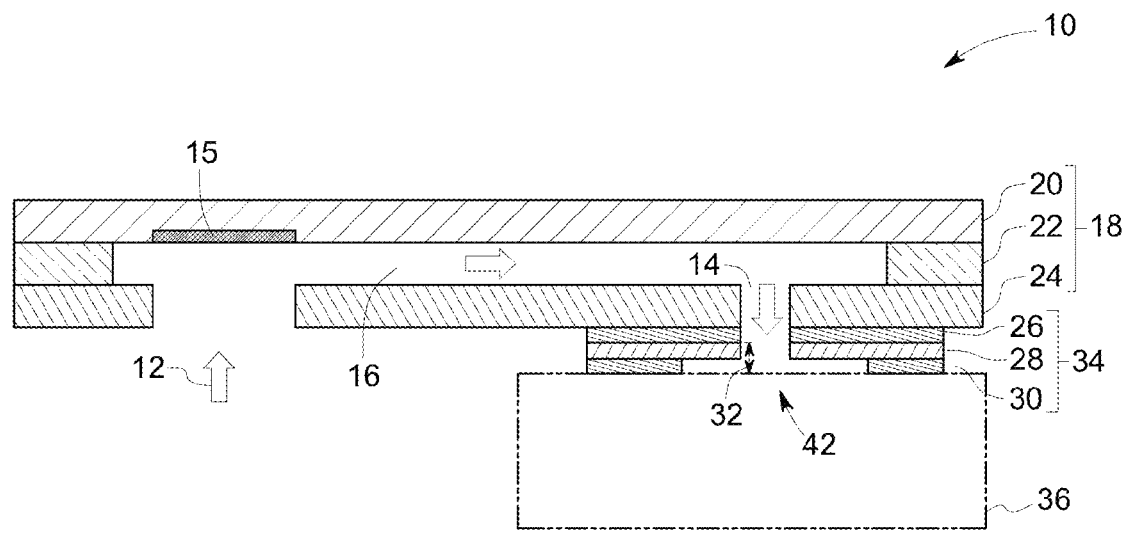
FIG. 1B is a schematic representation of a cross-sectional view of another example embodiment of an integrated device for sample collection and transfer.

FIG. 1 illustrates an exploded view of a design of an example of an integrated device for sample collection and transfer 10. The sample collection and transfer device 10 includes a capillary 18 comprising a first layer 20, a middle layer 22 and a second layer 24. The first layer further comprises an inlet 12, and the second layer 24 comprises an outlet 14, wherein the capillary channel is 16. The device 10 further comprises an interface assembly 34, including a third layer 26, fourth layer 28 and fifth layer 30, wherein a flow path 32 is connecting the capillary outlet to the substrate, through the interface assembly. In certain embodiments, the interface assembly 34 may be disposed on a substrate 36. At least a portion of a device 10 may be disposed on the substrate 36. In one or more embodiments, the capillary 18 and the interface assembly 34 comprise a multilayer structure which may be laminated by one or more intervening adhesive layers. In some embodiments, the substrate is operationally coupled to the device. In these embodiments, the substrate may be attached during the sample collection and transfer and detached from the device when the operation is over. In one example, the capillary channel is a fluidic channel 16. The capillary channel may be a microfluidic channel. The fluidic channel 16 facilitates fluidic communication between a fluid source (not shown) and the substrate 36. The fluid source may be external to the sample collection and transfer device 10.

In the illustrated embodiment, the fluidic channel 16 may traverse from the inlet to the outlet, wherein the outlet is further connected to the substrate 36 through interface assembly. An air gap may be present at the junction of the interface assembly 34 and the application zone of the substrate 36. The capillary force and hydrophilic force generated by the capillary channel 16 and interface assembly 34 may be configured to provide uniform pressure on the sample around the junction of the interface assembly 34 and the application zone 42 of the substrate 36. The uniform pressure may enable the fluid to overcome the obstruction created by the air gap, and move forward towards the substrate 36. In operation, an external force may be applied to the device 10 by gentle tapping to the device to complete the sample transfer. The force applied on the device 10 may cause the fluid sample to push against the air gap or internal friction of the device and ensure reaching to the substrate 36. It should be noted that the size and shape of the capillary 18 may be varied depending on a size and shape desirable for the application zone based on a given application or use of the device.

Various layers of the integrated device for sample collection and transfer 10 may be made of plastic. In some embodiments, some or all of the components of the sample collection and transfer device 10 may be disposable in nature. By way of example, the capillary 18 of the sample collection and transfer device 10 may be disposable in nature. In some embodiments, the capillary 18 and the interface assembly 34 may be made using additive manufacturing. Advantageously, additive manufacturing techniques may enable the device to take the form of a single structure for each key component (e.g., capillary) rather than multilayer components. In one example, the sample collection and transfer device 10 may be made using low cost and high throughput methods, such as, but not limited to, injection molding.

In certain embodiments, the sample collection and transfer device 10 may be operatively coupled to a sample extraction device (not shown). The sample collection and transfer device 10 (FIG. 1) may be configured to facilitate consistent sample application to the sample substrate 36 by a trained or untrained user. In one embodiment, after transferring the biological sample, at least a portion of the sample collection device may be discarded. The dotted line of the substrate represents the fact that the substrate 36 may be coupled to the device 10 operationally, and not pre-attached to the device 10.

Figure 2:
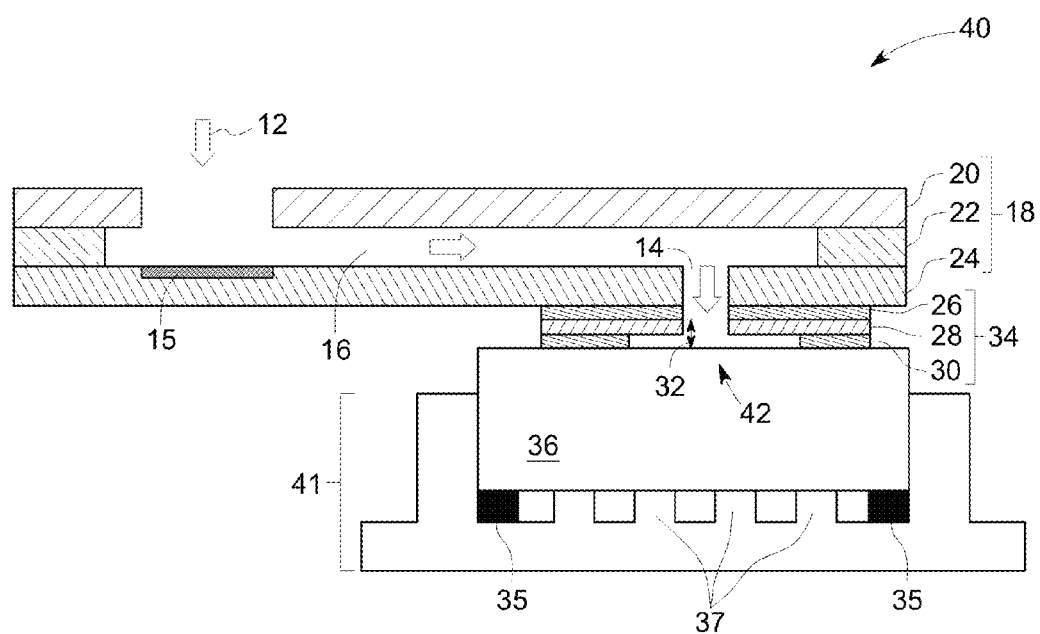
FIG. 2 is a schematic representation of a cross-sectional view of an example embodiment of a system comprising an integrated device for sample collection and transfer, a substrate in a substrate frame and a substrate cover.

FIG. 2 represents a system configuration 40, wherein the collection and transfer device 10 may be coupled to a substrate 36 (solid line), wherein the substrate is pre-attached to the device and form the system. The system further comprises a substrate frame 41 comprising a device holder 43, a flexible hinge 45 and a substrate cover 38. The substrate frame 41 enables user to handle the substrate, provides rigidity to the system and helps protect the substrate from contamination. In some embodiments, the system may further comprise a substrate cover or protective cover 38 (as shown in FIG. 3B). In operation, in the sample collection device 10 the substrate cover 38 exposes the sample substrate 36 for collecting the sample and the substrate cover 38 automatically folds to protect the substrate. Upon removal of the integrated device from the substrate frame 41 by the user, the substrate cover 38 is repositioned over the sample substrate 36 for handling protection. The substrate frame 41 comprises adhesive pads 35 which help to adhere the substrate on the frame 38 and support pillars 37 to provide enough support to the substrate for proper positioning on the substrate frame (see FIG. 2).

Whereas, in the illustrated embodiment of FIG. 2, the sample substrate 36 is covered for handling, transport and sample elution. In one embodiment, when the sample collection and transfer device 10 is operatively coupled to the analysis unit, the substrate cover 38 (shown in FIG. 3 B) may be used to cover the sample disposed in the sample application zone 42 of the substrate 36. By way of example, when a portion of the sample collection and transfer device 10 is operatively coupled to an external device (not shown)

the substrate cover 38 may be used to cover the sample during analysis. In another embodiment, after analysis, when required, the folding substrate cover 38 may be moved to expose the sample. It should be noted that the external device may be any device or instrument that is external to the sample collection and transfer device. Non-limiting examples of the external device may include a fluidic device (e.g., a microfluidic device), a storage and extraction device, an analysis instrument, a device configured to mate with a portion of the sample collection and transfer device 10, or combinations thereof. In a particular example, the external device may be a microfluidic device.

Figure 3A:
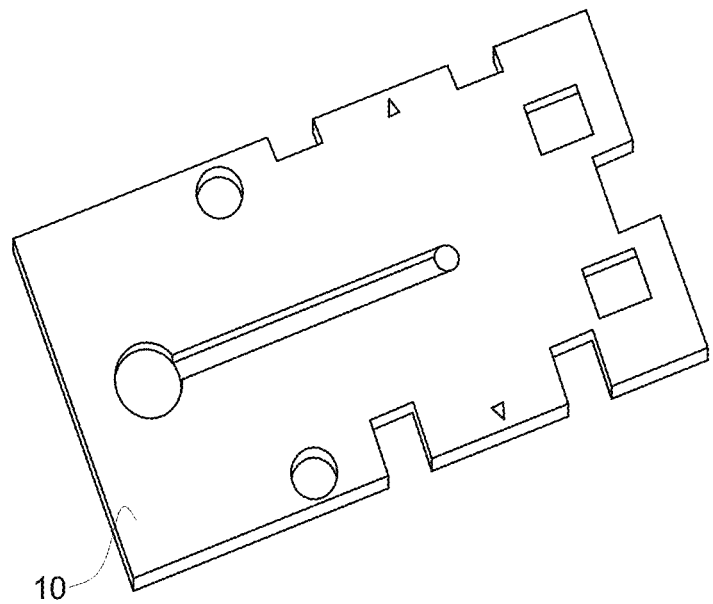
FIG. 3A is a schematic representation of a top view of an example of an integrated device comprising a capillary channel.
Figure 3B:
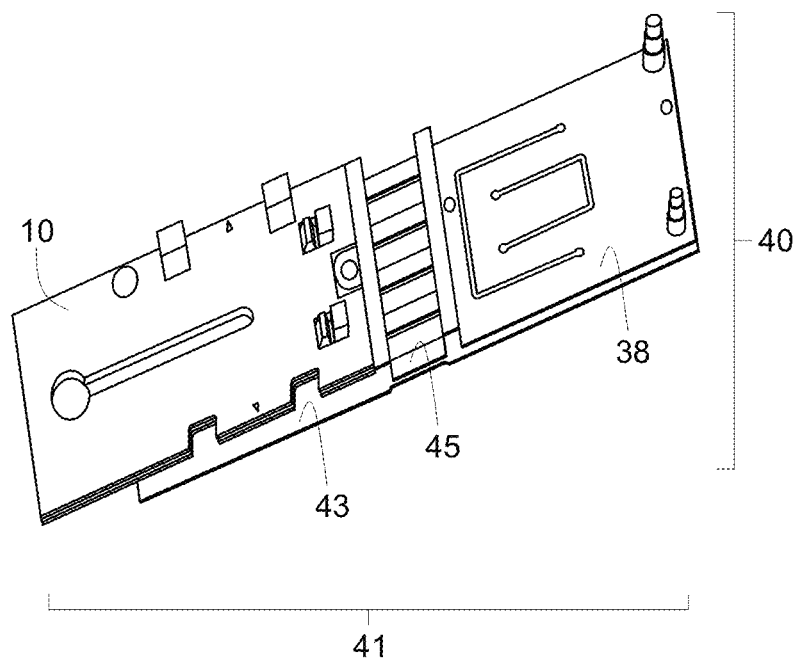
FIG. 3B is a schematic representation of a top view of an example of a system comprising an integrated device, a substrate, a substrate frame, a flexible hinge and a substrate cover to enclose the substrate.

FIG. 3A shows an exploded view of an integrated device 10 and FIG. 3B shows a system 40. FIG. 3B further illustrates a perspective view of an example of a system comprising an integrated device 10 for sample collection and transfer, wherein the integrated device 10 is coupled to a substrate 36 (not shown). The entire substrate 36 is located on the substrate frame 41. The substrate frame 41 comprises a device holder 43, a flexible hinge 45, and a protective cover 38. The flexible hinge 45 is configured such that the substrate cover 38 is foldable and can cover the substrate 36 when required.

Figure 4A:
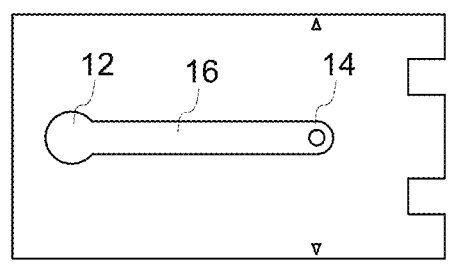
FIGS. 4A and 4B are schematic representations of a top view and a bottom view of an example of a capillary channel disposed on a substrate, respectively.
Figure 4B:
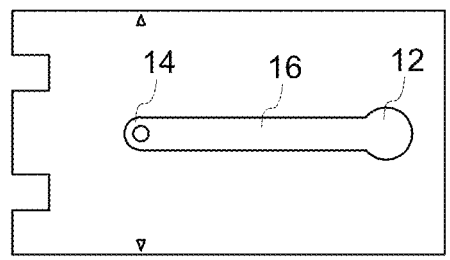
Figures 5A, 5C:
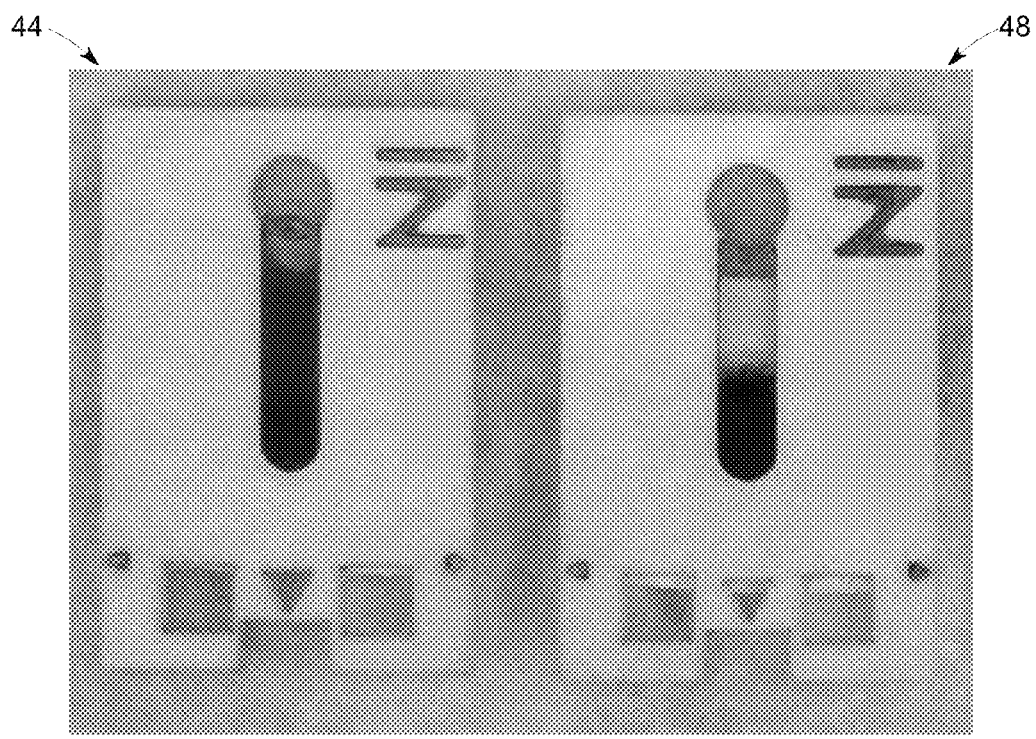
FIGS. 5A and 5B are images of a capillary action of a blood sample and a substrate after transferring the blood sample, respectively, using a device without having an interface assembly.
FIGS. 5C and 5D are top view and bottom view, respectively, of a capillary action of a blood sample and a substrate after transferring the blood sample using an integrated device comprising an interface assembly.
Figures 5B, 5D:
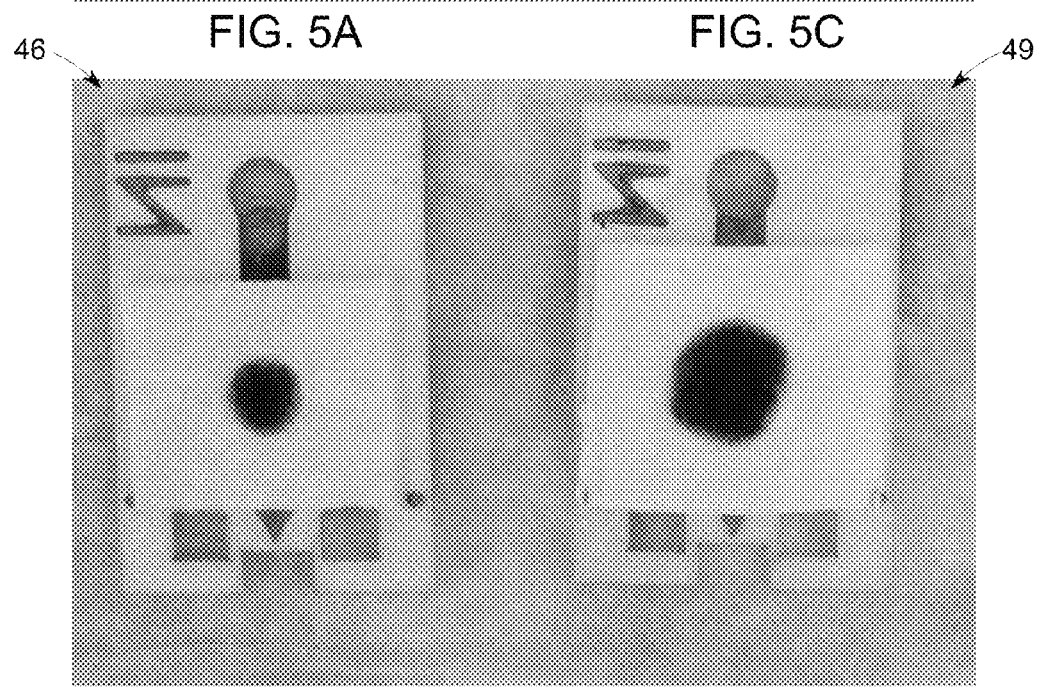

A top view and bottom view of an integrated device are illustrated in FIGS. 4A and 4B, respectively. The device comprising an inlet 12, a capillary channel 16 and an outlet 14 and the device is viewed from inlet side (FIG. 4A) and also viewed from outlet side (FIG. 4B). FIG. 5A illustrates a 50 µL capillary action for collection and transfer of the blood to a substrate using a device 44 comprising a capillary channel with only the $5^{th}$ layer (single layer gasket) but not the $3^{rd}$ and $4^{th}$ layer. FIG. 5C illustrates a 50 µL capillary action for collection and transfer of the blood to a substrate using an integrated device 48 comprising a capillary channel and an interface assembly (with $3^{rd}$, $4^{th}$, and $5^{th}$ layers). FIG. 5D shows the complete transfer of the blood to the substrate 49 corresponding to device 48 of FIG. 5C. FIG. 5B shows an incomplete transfer of blood to the substrate 46 (corresponding to device of FIG. 5A, 44) due to the slow transfer speed and subsequent clotting of the blood.

Figure 6D:
Figure 6E:
Figure 6F:

FIGS. 6A, 6B and 6C illustrate alternative embodiments of integrated device 10 for the sample collection and transfer using different gasket designs. In the illustrated embodiments, the images show the devices after passing the blood sample through the capillary and transferred to the substrate, wherein different patterns of the transferred blood sample is generated on the substrates due to different gasket designs, as shown in FIGS. 6D, 6E and 6F. The gasket with more channels shows quicker transfer of the blood sample with uniform distribution (FIG. 6D), wherein the gaskets having fewer number of channels (FIG. 6E) show quick transfer but non-uniform distribution, and the gasket without channel shows slow transfer with non-uniform distribution (FIG. 6F). Different gasket patterns are shown in inset of FIGS. 6A, 6B and 6C and the gasket designs influence the transfer rate and uniform distribution of the sample significantly. After transferring the blood sample to an RNA stabilizing membrane, the stability of the blood derived RNA was tested, which shows 6.8-7.0 RNA score after five days of incubation at room temperature. The material used for the integrated device does not affect the stability of the components of the transferred blood sample, such as RNA.

Embodiments of a method for sample collection and transfer, comprises providing an integrated device and, contacting the integrated device to a substrate comprising an absorbent material. In these embodiments, the method further comprises applying a fluid sample to the capillary inlet of the integrated device, wherein the fluid sample is transported from the inlet to the outlet of the capillary. The fluid sample may further be transferred from the integrated device to the substrate through the flow path of the interface assembly; wherein the sample collection and transfer is achieved in at least 5 second, in some other embodiment the sample collection and transfer is achieved in at least 10 seconds.

As noted, the sample collection and transfer is achieved in at least 5 seconds or 10 seconds by using the integrated device, which refers that the minimum run time of the device is 5 seconds or 10 seconds. The term "run time" refers to herein as a time taken by the device starting from a sample fluid collection and ends with a complete transfer of the fluid sample to a substrate or other device. The upper limit of the run time, by which the collection and transfer of the sample is desired to be completed may be the span of time, wherein the sample fluid retains its physical and chemical structures and functions. For example, when the sample fluid is a blood sample, the upper limit of the run time is determined depending on the time required for a blood sample to coagulate. Typically, the expected range of clotting time for blood is 4-10 minutes. The coagulated blood may clog the channel and the substrate and may result in erroneous data for analyte detection or downstream analysis. The blood sample may coagulate during collection and transfer of the sample. The integrated device facilitates the fast collection and transfer of the fluid sample ensuring no blood coagulation occurs during the run time (collection and transfer) of the device. In some embodiments, the sample collection and transfer is achieved in a time between 5 seconds to 120 seconds. In some other embodiments, the sample collection and transfer is achieved in a time between 10 seconds and 120 seconds (2 minutes).

The method further comprises detaching the integrated device from the fluid source, wherein the capillary is filled with the fluid sample. In other embodiments, the method further comprises detaching the integrated device from the substrate after complete transfer of the fluid sample. The method further comprises analyzing the substrate, wherein the substrate comprises the sample fluid transferred from the device. For example, the amount of blood collected and transferred to the substrate is homogenously spread over the substrate, wherein the sample from the substrate is tested for a plurality of times for various applications.

In an example, the user may apply their pricked finger to a loading pad located at the inlet of the integrated device, wherein the blood sample may flow into the capillary through the inlet, due to both capillary force and the hydrophilic force exerted by the first layer and the hydrophilic loading pad. When the blood flow reaches the outlet, the flow may briefly pause due to presence of an air-gap at the junction of the outer most point of the flow path of the interface assembly and an absorptive material, such as a substrate. The air-gap formed at the junction of the interface assembly and the substrate is large enough to prevent sample to transfer from the integrated device to the substrate via capillary force. The capillary of the integrated device may be made of a material that allows the user to see the volume of blood intake by the capillary and the movement of the blood flow. When the blood flow reaches at the end of the capillary such that the capillary is filled with the blood sample, the user may remove the source of blood sample (such as finger) from the device inlet and gently tap the device to create a pressure to overcome the resistance generated by the air-gap. The pressure created by gentle tapping to the device inlet ensures absorbing the entire metered blood volume by the substrate, e.g. FTA-paper. The air-gap may be replaced by functional membranes and materials, e.g. to filter out certain blood components. The diameter and shape of the capillary outlet affects the time required for transferring the sample and the shape of the blood-spot on the substrate. To mitigate particular need, the shape, size and design of the channels on the gasket may vary. When the blood is transferred to the substrate completely, the user may remove the integrated device to detach the capillary from the substrate.

FIG. 7 illustrates a flow chart 50 of an example method for collecting a sample, transferring the sample to a sample substrate, storing the sample for analysis, and analyzing the sample. At block 52, the method may commence by providing an integrated device. The step of providing the integrated device may include disposing integrated device to the sample substrate or substrate holder of the sample storage and extraction device. Moreover, in embodiments where the integrated device and the sample storage and extraction device do not form an integral structure, the integrated device may be coupled to the substrate after collecting the sample. The step of coupling the sample storage and extraction device to the integrated device may include operatively coupling the sample storage and extraction device to the sample collection device.

At block 54, a physical contact may be provided between at least a portion of a substrate and the integrated device. Referring back to FIGS. 1-2, in some embodiments, when the integrated device for sample collection and transfer 10 is coupled to the substrate or operationally coupled to the substrate, the substrate cover 38 may be configured to fold back, thereby exposing the sample substrate 36 to the fluidic sample.

The fluid sample may be applied to the integrated device for collecting the sample from a source. In some embodiments, the integrated device and a sample storage substrate may form an integral monolithic structure. Whereas, in another embodiment, the integrated device and the sample storage substrate may be removably coupled to one another.

At block 56, at least a portion of the sample may be transported from the inlet of the capillary to the capillary outlet. After the fluid sample, such as blood is transferred from the finger stick to the capillary inlet, the fluid further flows towards the capillary outlet. The transfer of the sample from the sample source to the sample substrate may be facilitated by applying a determined amount of pressure on the capillary of the integrated device. As noted, a gentle tap or mild shaking of the capillary may be used to overcome the air gap at the junction of the integrated device and the substrate. In one example, the pressure applied to the integrated device may enable the fluid to move towards the substrate and transferred completely to the sample substrate.

In block 58, the fluid transferred from the outlet of the capillary to the interface assembly. As the interface assembly layers are specifically hydrophilic in nature, a hydrophilic force act on the fluid passes through the flow path in a lesser time compared to a standard tubing or channel. Moreover, the interface assembly comprises a gasket, wherein the gasket may comprise multiple channels. The multiple channels of the gasket helps in quick transferring of the blood sample with uniform distribution, as shown in FIG. 5A. The layer by layer arrangement of interface assembly influences the transfer rate and uniform distribution of the sample significantly. In block 59, the method further comprises detaching the integrated device from the substrate after complete transfer of the fluid sample to the substrate.

In block 60, the fluid sample is transferred from the interface assembly to the substrate. The positioning of the interface assembly on the sample substrate may be such that the sample transferred to an area of extraction on the substrate, and the integrated device outlet and the substrate are aligned with accordingly.

Optionally, the sample storage, extraction and analysis device may be coupled to the integrated device or decoupled from the integrated device. At block 62, at least a portion of the sample substrate having the transferred sample fluid may be covered for storage and further analysis. In one example, the substrate may be covered with the substrate cover for storage. The transferred sample may be stored either by refrigeration or at room temperature. In particular, the substrate frame may be closed immediately before or after decoupling the substrate frame or the substrate from the integrated device. In an example embodiment, upon decoupling the substrate cover 38 (see FIG. 2) may be configured to slide on the substrate holder or substrate frame (not shown) to cover at least the portion of the sample substrate having the sample.

Optionally, at block 62, the sample may be allowed to dry for a determined period of time. Further, the sample storage device may be dispatched to a desirable location or stored in the lab for analysis of the sample. The dried sample may be stored in refrigerator or at room temperature followed by drying the sample for further analysis.

In block 62, the steps for processing and analyzing the sample disposed on the sample substrate may be performed. The sample may be extracted and analyzed. The step of analyzing may include identifying one or more components of the sample. Further, the step of analyzing may include quantifying an amount of one or more substances in the collected sample fluid. In methods in which the sample comprises blood or other various types of biological materials, the analyzing step may comprise identifying one or more components of the sample.

The methods and systems of the disclosure may analyze the samples and materials extracted from the samples for many different purposes using a variety of analyzing systems such as, but not limited to, immunoassays (e.g. to identify the presence or absence of a component), liquid chromatography with UV detection (e.g. to characterize and quantify components), qPCR, RT-PCR, DNA microarrays, isothermal nucleic acid amplification and liquid chromatography with mass spectrometry (e.g. to identify and/or quantify components).

In some embodiments, for record keeping and traceability, the present device may also comprise an identification label (such as conventional bar coding). In one example, the identification label may be disposed on the integrated device and the substrate for sample storage.

The integrated device for sample collection and transfer is user friendly and easy-to-use for point of care solutions that may require one or more of sample collection, sample transfer, sample storage, elution through the sample substrate, and device integration. The single-use and disposable nature of the integrated device reduces the probability of contamination of the sample, which further minimizes infection of the users.

EXAMPLES

Example 1

Developing an Integrated Device Prototype

The integrated device for collection and transfer of sample fluid was developed using multiple plastic layers.

The multiple layers of the device were laminated together to provide an integrated structure of the device. The unbreakable features, inexpensive fabrication, and easy integration capability with the substrate are reasons for selection of the laminated capillary for the device prototype. The integrated device was made with a laminated multi-layered structure, including a first layer of 0.173 mm thick, 9960 hydrophilic polyester film from 3M™, a middle layer of 0.25 mm thick, Lexan 561 film from SABIC and a second layer of 0.173 mm thick, 9960 hydrophilic polyester film from 3M™. 0.125 mm thick AR 8939 double sided adhesive films were used in between each of the layers for laminating the capillary. The fluidic channel was created by laser cutting of the middle layer and the adjacent adhesive layers. The cut middle layer was laminated with the first layer. The inlet and outlet holes were laser cut in the first layer and second layer, respectively.

The capillary was connected to a substrate via a gasket assembly made of a pressure sensitive adhesive (PSA), such as 50 μm thick 200 MP PSA from 3M™, followed by a film layer from Adhesive Research ARflow™ (hydrophilic pressure sensitive adhesive on Polyester), and a patterned layer (see FIG. 3 for designs) of 50 μm thick 200 MP PSA from 3M™ (see FIG. 1, layers 26, 28 and 30 for reference)

Through the course of designing the capillary, several different channel heights, channel width, outlet diameter, diameter of a loading pad, and channel shapes were tested. Testing with fresh animal blood (without adding anticoagulant) optimized the channel height to avoid coagulation in the capillary. A channel height of 127 μm led to frequent coagulation in the capillary while a channel height of 508 μm was able to avoid coagulation in the channel.

Experiments with human blood showed that a channel having an outlet diameter smaller in size than the channel width increased the speed of blood transfer to a substrate. The optimized channel used for this experiment had an inlet diameter of 6 mm, outlet diameter of 2.25 mm, channel width of 4.25 mm and channel height of 0.508 mm. Presumably, this is because the blood can enter the outlet from the entire perimeter. With these features it takes less than 45 seconds to collect and deposit 35 uL of blood. Image analysis indicated that the final size of the blood spot has a CV<5%. Examples of the blood spots created using capillaries are shown in FIG. 6D.

Example 2

Sample Application to a Substrate Using the Integrated Device Prototype and Analysis A drop of blood was pipetted onto a piece of parafilm to simulate a pricked finger. The capillary prototype was tested with a commercial sample of human blood treated with the anticoagulant Citrate Phosphate Dextrose (CPD), and a sample of fresh rat blood. The blood drop touched the loading pad of the capillary inlet and was drawn to the capillary channel. When the blood reached at the end of the capillary channel, the user removed the capillary from the blood sample. The blood sample in the capillary was transferred to the substrate. After complete transfer from the capillary (when the capillary was empty), the integrated device prototype was removed from the substrate. The transfer of blood on the substrate is shown in FIGS. 5B and 5D. The transferred blood spot was allowed to dry and was analyzed further.

Example 3

Sample Fluid (Blood) Collection and Transfer to a Substrate Located on the Substrate Frame The capillary, as shown in FIGS. 4 A, and 4 B, was designed to be compatible with the substrate frame. The capillary was manufactured by laser cutting the middle layer, and the design was adapted to a punching based manufacturing method, which reduced costs and eliminated issues associated with laser cutting residues that impeded capillary flow.

FIGS. 5 A and 5 C showed two different steps of capillary flow for collection and transfer of blood sample using two different devices, one is without interface assembly and another with interface assembly. Both were designed for 50 uL of blood sample. The blood spotting on the substrate for each case was demonstrated in FIGS. 5 B and 5 D, respectively. The complete transfer of blood to the substrate is shown in FIGS. 6 A-C using different gasket design.

Example 4

Effect on Sample Transfer Using Different Gasket Patterns and RNA Analysis

Gaskets with and without channels were used in different prototype of the integrated device, and the transfer rate, transfer efficiency, uniformity of sample after transfer were determined. A drop of fresh rodent blood sample from a tail vein was pipetted onto each of the device prototype having different gasket designs. The blood drop touched the inlet of the capillary and was drawn to the capillary channel. When the blood reached at the end of the capillary channel, the blood sample was transferred to the substrate, wherein the capillary was detached from the substrate such that the capillary was no longer in contact with the blood sample transferred to the substrate. After complete transfer from the capillary (when the capillary was empty), the integrated device prototypes were removed from the corresponding substrates. The transferred blood spot were allowed to dry.

FIGS. 6 A-C illustrate blood sample transferred using different gasket designs. The gasket with more number of channels showed quick transfer of the blood sample with uniform distribution as shown in FIG. 6 D for device of FIG. 6A, wherein the gaskets with fewer number of channels as shown in FIG. 6 E for device of FIG. 6B, FIG. 6 F showed quick transfer but non-uniform distribution, and the gasket without channel showed slow transfer with non-uniform distribution (for device of FIG. 6C). The gasket pattern significantly influenced the transfer rate and uniform distribution of the sample.

After transferring the blood sample, the intactness of the blood derived RNA was tested for each case using a RNA Pico Chip with the Agilent 2100 Bioanalyzer. The data indicate a RIN score of 6.8-7.0 after five days of incubation at room temperature. This indicates that the material used for the device does not affect the stability of the components of the transferred blood sample, such as RNA.

While only certain elements of the invention have been illustrated and described herein, many modifications and changes will occur to those skilled in the art. It is, therefore, to be understood that the appended claims are intended to cover all such modifications and changes as fall within the scope of the invention.

The invention claimed is:

1. An integrated device for a sample collection and transfer, comprising:
   a capillary channel disposed between a first layer and a second layer, wherein the first layer comprises a hydrophilic layer comprising a fluid inlet for receiving a sample fluid to the capillary channel, wherein the capillary channel comprises an inner surface and an outer surface; and an outlet for allowing the sample fluid to flow out of the capillary channel; and
   an interface assembly comprising: a third layer comprising an adhesive material, a fourth layer comprising a hydrophilic material, a fifth layer comprising a patterned adhesive material, and a flow path, wherein the third layer is disposed on the fourth layer and the fourth layer is disposed on the fifth layer;
   wherein the interface assembly is disposed on the outer surface of the capillary, at a determining position relative to the outlet, such that the capillary is in contact with the third layer of the interface assembly and the outlet is in contact with the flow path of the interface assembly for transfering the sample fluid out of the integrated device;
   wherein the integrated device is coupled to a substrate and configured to transfer the sample fluid to the substrate.

2. The integrated device of claim 1, wherein the first layer comprises the outlet.

3. The integrated device of claim 1, wherein the second layer comprises the outlet.

4. The integrated device of claim 1 further comprising a loading pad with a first diameter.

5. The integrated device of claim 1, wherein the capillary channel has a channel width and the outlet has a second diameter.

6. The integrated device of claim 4, wherein the channel width is greater than the second diameter.

7. The integrated device of claim 4, wherein the channel width is in a range between 3 to 50 mm and the second diameter is in a range between 0.5 to 10 mm.

8. The integrated device of claim 1, wherein the capillary channel has a length in a range from 5 mm to 200 mm.

9. The integrated device of claim 1, wherein the capillary channel is made of a material selected from polymer, metal, glass or combinations thereof.

10. The integrated device of claim 1, wherein the first layer comprises a hydrophilic film with a water contact angle of less than 60 degree.

11. The integrated device of claim 1, wherein the first layer comprises a polymer.

12. The integrated device of claim 1, wherein the capillary channel, inlet and outlet are formed by laser drilling, rotation cutting, ballistic pressing or combination thereof.

13. The integrated device of claim 1, wherein the determining position is configured to inline the outlet of the capillary with the flow path of the interface assembly.

14. The integrated device of claim 1, wherein the third layer comprises a pressure sensitive adhesive.

15. The integrated device of claim 1, wherein the fourth layer comprises a hydrophilic material, polymeic material, a material with hydrophilic coatings, a material with hydrophilic surface treatment or combinations thereof.

16. The integrated device of claim 1, wherein the fifth layer comprises a gasket made of pressure sensitive adhesive material.

17. The integrated device of claim 15, wherein the pressure sensitive adhesive material of the gasket comprises acrylics, butyl rubber, ethylene-vinyl acetate (EVA), natural rubber; nitriles; silicone rubbers, styrene block copolymers (SBC), styrene-butadiene-styrene (SBS), styrene-ethylene/butyl ene-styrene (SEBS), styrene-ethylene/propylene (SEP), styrene-isoprene-styrene (SIS), vinyl ethers or combinations thereof.

18. The integrated device of claim 1, further comprising a hydrophilic pad adjacent to the inlet to facilitate receiving the sample fluid to the capillary.

19. The integrated device of claim 1, wherein the substrate comprises cellulose, nitrocellulose, modified porous nitrocellulose or cellulose based substrates, polyethyleneglycol-modified nitrocellulose, a cellulose acetate membrane, a nitrocellulose mixed ester membrane, a glass fiber, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, glass fiber membranes, quartz fiber membranes or a combination thereof.

20. The integrated device of claim 1, wherein the substrate comprises one or more dried reagents impregnated therein.

21. The integrated device of claim 20, wherein the dried reagents comprise protein stabilizing reganets, nucleic acid stabilizing reagents, cell-lysis reagents or combinations thereof.

22. The integrated device of claim 1, wherein the substrate is disposed on a substrate frame.

23. The integrated device of claim 1, wherein the device is disposable or re-usable.

24. A system, comprising:
   a substrate; and
   an integrated device comprising:
      a capillary channel disposed between a first layer and a second layer, wherein the first layer comprises a hydrophilic layer comprising a fluid inlet for receiving a sample fluid to the capillary channel and wherein the capillary channel comprises an inner surface and an outer surface; and an outlet connected to the capillary channel; and
      an interface assembly comprising: a third layer comprising an adhesive material, a fourth layer comprising a hydrophilic material, a fifth layer comprising a patterned adhesive material and a flow path, wherein the third layer is disposed on the fourth layer and the fourth layer is disposed on the fifth layer;
      wherein the interface assembly is disposed on the outer surface of the capillary, at a determining position relative to the outlet, such that the capillary channel is in connection with the flow path of the interface assembly;
      wherein the integrated device is operatively coupled to the substrate such that substrate is in contact with the interface assembly for transferring the sample fluid from the integrated device to the substrate.

25. The system of claim 24, wherein the system further comprises a substrate frame having a substrate region configured to receive the substrate.

26. The system of claim 24, further coupled to an external device, wherein the external device comprises a fluidic device, an analytical instrument, or both.

27. A method for sample collection and transfer, comprising:
   providing an integrated device, wherein the device comprises:

a capillary channel disposed between a first layer and a second layer, wherein the first layer comprises a hydrophilic layer comprising a fluid inlet for receiving a sample fluid to the capillary channel, wherein the capillary channel comprises an inner surface and an outer surface; and an outlet for allowing the fluid to flow out from the device; and an interface assembly comprising: a third layer comprising an adhesive material, a fourth layer comprising a hydrophilic material, a fifth layer comprising a patterned adhesive material, and a flow path, wherein the third layer is disposed on the fourth layer and the fourth layer is disposed on the fifth layer; wherein the interface assembly is disposed on the outer surface of the capillary, at a determining position relative to the outlet, such that the capillary channel is in connection with the flow path of the interface assembly;

contacting the integrated device to a substrate comprising an absorbent material;

applying a fluid sample to the capillary inlet of the integrated device, wherein the fluid sample is transported from the inlet to the outlet of the capillary; and transferring the fluid from the integrated device to the substrate through the flow path of the interface assembly;

wherein the sample collection and transfer is achieved at least in 10 seconds.

28. The method of claim 27, wherein the sample collection and transfer is achieved in a time between 10 seconds and 120 seconds.

29. The method of claim 27, further comprising detaching the integrated device from the substrate after complete transfer of the sample to the substrate.

30. The method of claim 27, further comprising analysing the substrate comprising the sample fluid transferred from the device.

31. The method of claim 27, wherein the substrate is configured to store the fluid sample.

32. A method for sample collection and transfer, comprising:

providing an integrated device, wherein the device comprises:

a capillary channel disposed between a first layer and a second layer, wherein the first layer comprises a hydrophilic layer comprising a fluid inlet for receiving a sample fluid to the capillary channel, wherein the capillary channel comprises an inner surface and an outer surface; and an outlet for driving out the sample fluid; and an interface assembly comprising: a third layer comprising an adhesive material, a fourth layer comprising a hydrophilic material, a fifth layer comprising a patterned adhesive material, and a flow path, wherein the third layer is disposed on the fourth layer and the fourth layer is disposed on the fifth layer; wherein the interface assembly is disposed on the outer surface of the capillary, at a determining position relative to the outlet, such that the capillary channel is in connection with the flow path of the interface assembly;

contacting the device to the substrate comprising an absorbent material;

applying a fluid sample to the capillary inlet of the integrated device, wherein the fluid sample is transported from the inlet to the outlet of the capillary; and transferring the fluid from the integrated device to the substrate through the flow path of the interface assembly, wherein the sample collection and transfer is achieved in at least 10 seconds; and analyzing a portion of the substrate comprising the fluid sample transferred from the device.

* * * * *